United States Patent [19]

Cheh et al.

[11] Patent Number: 4,780,116

[45] Date of Patent: Oct. 25, 1988

[54] LOW TEMPERATURE PREPARATIVE GAS CHROMATOGRAPHY APPARATUS

[76] Inventors: Christopher H. Cheh, 4239 Anworld Place, Mississauga, Ontario, Canada, L4W 2W1; Samuel H. Hawthorne, 3 Farmington Drive, Brampton, Ontario, Canada, L6W 2V1; Ronald E. Massey, 3135 Bentworth Drive, Burlington, Ontario, Canada, L7M 1V9; Otto K. Kveton, 25 Dacre Crescent, Toronto, Ontario, Canada, M6S 2W2; Savtantar K. Sood, 97 Banting Crescent, Brampton, Ontario, Canada, L6Y 2M3

[21] Appl. No.: 123,370

[22] Filed: Nov. 20, 1987

[51] Int. Cl.$^4$ ............... B01D 15/08; B01D 53/04
[52] U.S. Cl. ............................ 55/386; 55/197; 55/208; 55/389
[58] Field of Search .............. 55/197, 208, 386, 389

[56] References Cited

U.S. PATENT DOCUMENTS

| 3,432,995 | 3/1969 | Saeger et al. | 55/208 X |
| 3,533,220 | 10/1970 | Espagno | 55/19 |
| 3,734,293 | 5/1973 | Biskis | 55/208 X |
| 4,010,100 | 3/1977 | Suslick | 55/67 |
| 4,123,236 | 10/1978 | Hirschfeld | 55/197 |
| 4,154,583 | 5/1979 | Farre et al. | 55/208 X |
| 4,469,496 | 9/1984 | Frischmuth | 55/197 |
| 4,515,528 | 5/1985 | Young | 55/208 X |

FOREIGN PATENT DOCUMENTS

| 1519978 | 8/1965 | Fed. Rep. of Germany. |
| 2149508 | 8/1971 | Fed. Rep. of Germany. |
| 60-27855 | 2/1985 | Japan. |
| 512426 | 1/1977 | U.S.S.R. | 55/197 |

Primary Examiner—Charles Hart
Attorney, Agent, or Firm—Ridout & Maybee

[57] ABSTRACT

A gas chromatography apparatus adapted for large scale separation of gases at low temperature comprises a column packed with a solid adsorbent and having a cooling tube being open at both ends extending centrally through its length. The column is suspended in a pressure vessel so that it may be totally immersed in a liquified gas coolant. The pressure vessel has heating means to maintain the coolant at its boiling point and thereby to regulate the temperature within the vessel by varying the pressure therein. The apparatus has particular application to the large scale separation of hydrogen isotopes.

27 Claims, 4 Drawing Sheets

LOW TEMPERATURE PREPARATIVE GAS CHROMATOGRAPHY APPARATUS

The present invention is a gas chromatography apparatus and, in particular, an apparatus for performing low temperature gas chromatography.

The invention is particularly suited to the gas chromatographic separation of mixtures of hydrogen isotope dimers, i.e., all or any of $H_2$, $D_2$, $T_2$, HD, HT and DT. The invention enables the separation of large quantities of gases such as mixtures of hydrogen isotopes, and is particularly useful for the large scale processing of tritium containing hydrogen isotopic mixtures used in fusion research facilities, and which will be used in fusion reactor facilities.

The apparatus of the invention may be used to carry out the method described and claimed in U.S. Pat. No. 4,732,581. A preferred embodiment of the apparatus is described below which has a design capacity of about 3 mol per day of separated hydrogen isotopes in respect of an equimolar mixture, and which has a much higher capacity for fusion fuel clean-up applications.

Uniform cooling of columns used in the invention is effected by providing the columns with a central tube through which the coolant can flow to cool the column centrally while at the same time coolant is contacting the exterior surface of the column. Thus, a column having a central tube is immersed in a bath of liquified gas coolant to provide rapid and even cooling of the adsorbent in the column. The temperature of the column is regulated by placing the column in a pressurized container and maintaining the liquified gas coolant at its boiling point. The boiling coolant creates sufficient agitation to provide rapid and even heat transfer from the column, and the pressurization of the container enables the boiling point of the coolant, and hence, the internal temperature of the container to be varied.

The total length of column used in the apparatus may be contained in several pressurized containers which may be at different tempertures. This arrangement allows successive gas mixtures to be injected into the column without waiting for the previous sample to be eluted. Apportioning the total length of the column among several pressurized containers maximizes the flexibility for using temperature programming and heart cutting techniques since the temperature of each container can be controlled independently.

When used for the large scale separation of hydrogen isotopes, the invention preferably comprises a column packed with a molecular sieve material. The column is preferably contained in at least two pressurized containers sized to allow the column portion contained therein to be completely submerged in a liquified gas, preferably liquid nitrogen. The chromatography of the hydrogen isotope mixture is accomplished using a pressurized stream of an inert carrier gas, preferably helium, at temperatures ranging from about 77 K. to about 125 K.. The column temperature in each pressure container is regulated by maintaining the liquified gas coolant at its boiling point. Heating means provided in each container enables the constant boiling of the coolant at the chosen pressure.

Accordingly, the present invention provides a low temperature gas chromatography apparatus, comprising a column packed with a solid adsorbent material, having an inlet and an outlet formed at either end so that a pressurized gas may be flowed through the column. The column has a tube being open at both ends which extends centrally through the length of the column. A pressure vessel sized to contain the column immersed in a liquified gas, has pressure regulating means, an inlet for liquified gas, and an inlet and an outlet for the gas being flowed through the column. Heating means are provided within the pressure vessel for increasing the temperature of the liquified gas contained in it.

The following description of a preferred embodiment of the invention relates to the use of the invention in a system for separating on a large scale a mixture of hydrogen isotopes, that is, a mixture of the six isotopic dimers of hydrogen mentioned above. In particular, the following description relates to the use of the invention in a system for fusion fuel clean-up where the hydrogen containing components are separated from the $D_2$, $T_2$ and DT components.

Figure 1:
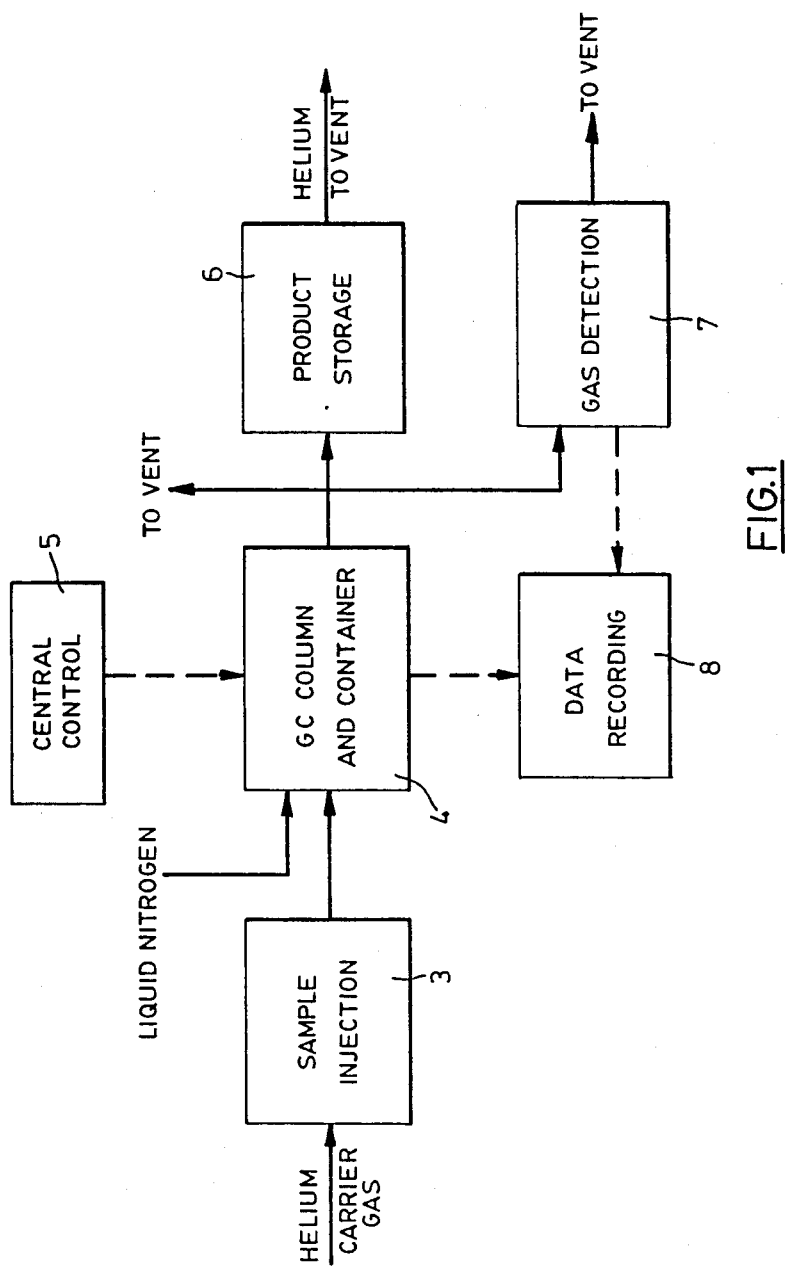
FIG. 1 is a schematic block diagram of the overall plant incorporating the invention in which solid lines denote flows and broken lines denote electrical connections.

As shown in FIG. 1, the apparatus of the invention forms a part of an overall gas processing system or plant. The plant is designed to handle a throughput of 3 mol/day of an equimolar mixture of H, D and T. The purity of $T_2$ separated from the mixture is $>99\%$ while the tritium content of $D_2$, HD and $H_2$ coming off the column is minimized as will be appreciated from the detailed description which follows.

The plant shown in FIG. 1 comprises several systems, namely, a sample injection system 3, a chromatography column system 4, a central control system 5, a product storage and secondary containment system 6, a detection system 7 and a data recording system 8.

Figure 2:
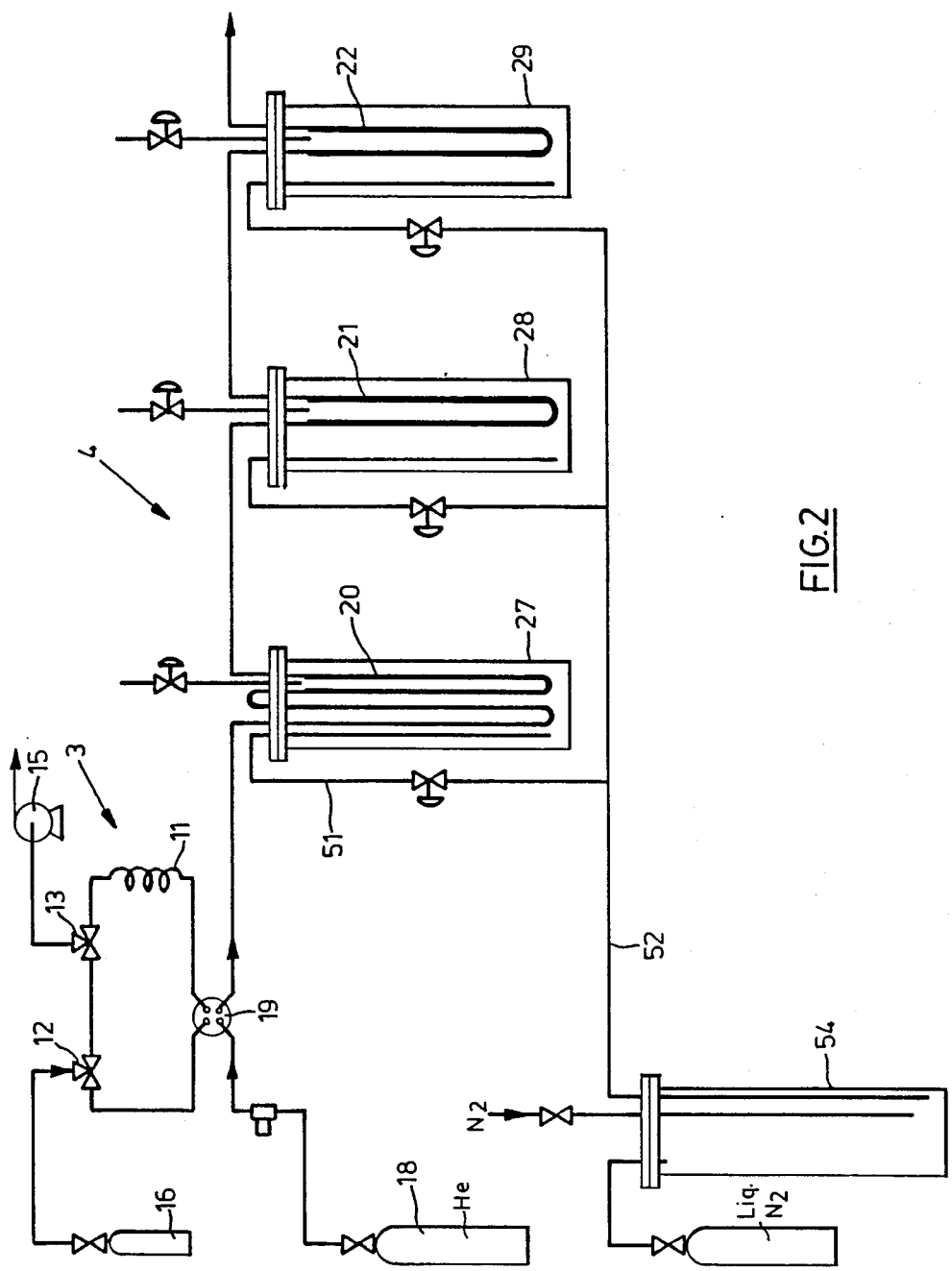
FIG. 2 is a schematic representation of the sample injection and chromatography systems.

The sample injection system 3 is schematically shown in FIG. 2 and comprises a sample loop 11 which is connected by means of two three-way valves 12 and 13 to a vacuum pump 15 and a sample cylinder 16 which contains the gas mixture to be separated. The sample loop 11 is also connected to the carrier gas supply 18 through a four-way valve 19. The sample loop 11 is evacuated by means of the vacuum pump 15 and then filled with sample from the cylinder 16 by appropriate operation of the valves 12 and 13. The sample in the loop 11 can then be injected into the column system 4 by switching the four-way valve 19 so that the carrier gas, preferably helium in this application, is routed from the supply tank 18 through the sample loop 11 and to the column system 4.

Figure 3:
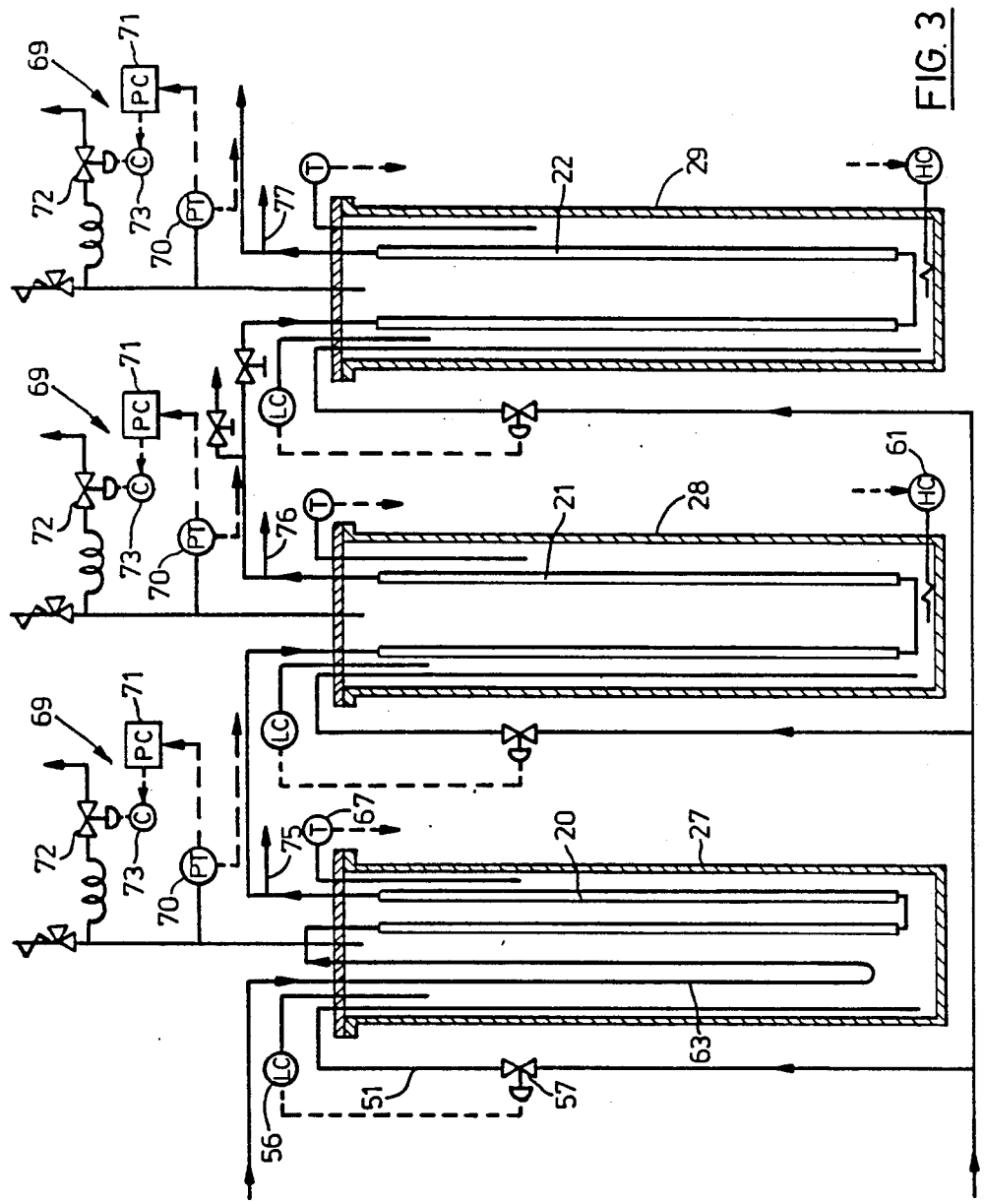
FIG. 3 is a schematic diagram of a preferred column system of the invention.

As shown in FIGS. 2 and 3 the column system 4 comprises a column divided into three sections 20, 21 and 22 each contained in a separate pressure vessel 27, 28 and 29. Each column section 20-22 contained in the vessels 27-29 comprises a plurality of straight column pieces joined in series. While the column system 4 described herein utilized two column pieces in the first section 20, four column pieces in the second section 21, and eight column pieces in the third section 22, the number of sections and the length of column in each section will vary with the particular application.

By dividing the column system 4 into two or more sections, temperature programming can be carried out on each section independently. Also, the entire quantity of the mixture being chromatographed need not pass through all sections of the column system 4. Especially in cases where a minor amount of material is to be separated from one or more major components, heart cutting or peak cutting techniques may be readily performed using the column system 4 having several column sections.

Separated products coming off any of the column sections 20–22 may be directed to the product storage or capture system 6, which in the case of hydrogen isotope separations are preferably uranium beds having a high affinity for hydrogen and its isotopes. It will be apparent to those skilled in this art that other types of "getter beds" may be used. A portion of the gas stream may be diverted between each column section 20–22 and from the exit stream leaving the column section 29, and such diverted streams may be analyzed by a detector 7.

The automated system records data from the column system 4, such as pressures and temperatures within the vessels 27–29, and records data from the detection system 7 at the data recording system 8. Data collection is governed by a computer in the central control system 5 where a central control console enables manual or fully automatic operation of the injection 3 and column 4 systems.

Figure 4:
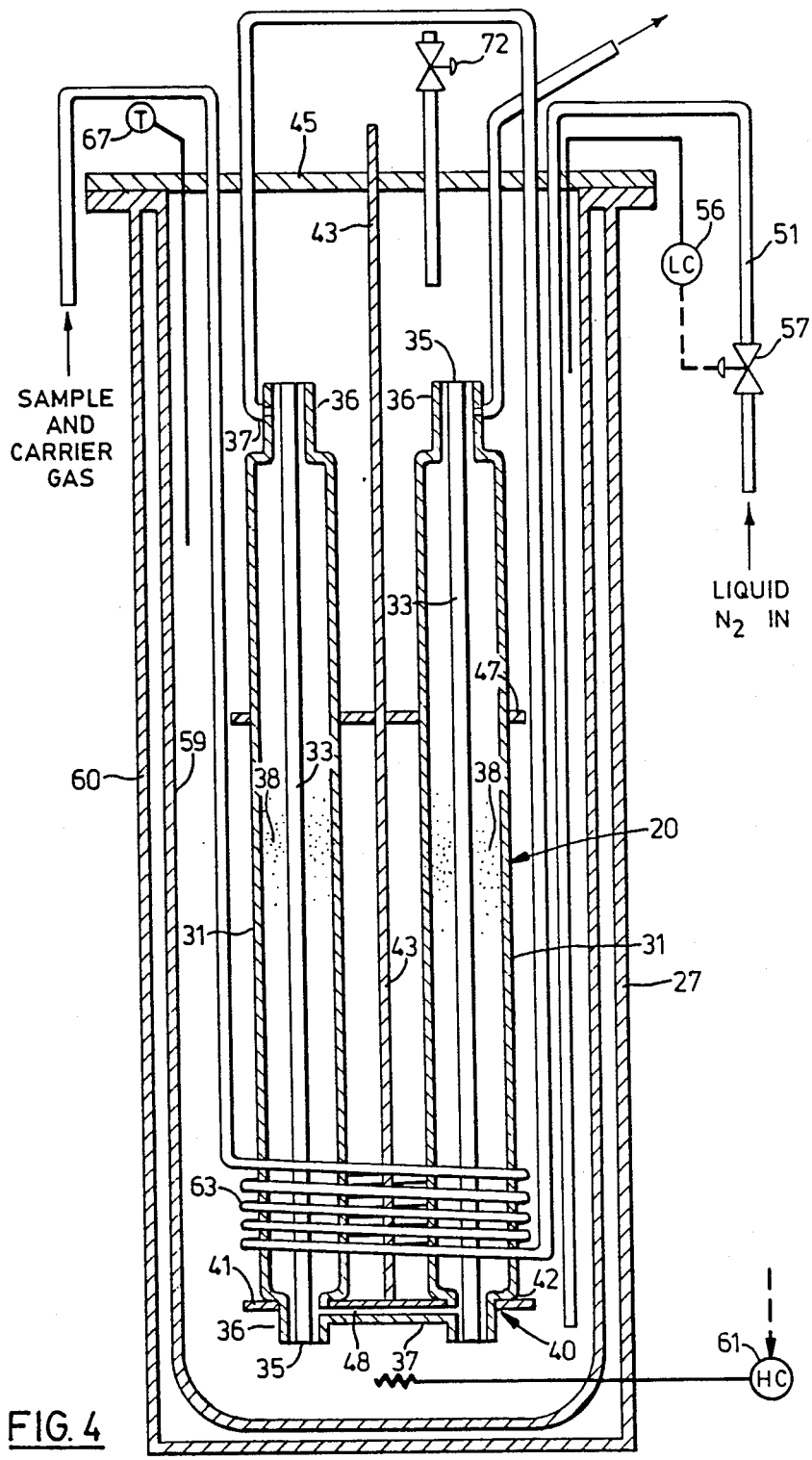
FIG. 4 is a sectional schematic view of a column in a pressure vessel in accordance with the invention.

A detailed view of the column section 20 and pressure vessel 27 is shown in FIG. 4. The column section 20 comprises two lengths of pipe 31 each having, in this case, an internal diameter of 3 inches and a length of 6 to 7 feet. The pipes 31 are preferably of stainless steel, but copper or other material may be suited for a particular application.

The pipes 31 are fitted with a central cooling tube 33, which in this embodiment is preferably a stainless steel tube having an internal diameter of $\frac{3}{4}$ inch. The cooling tube 33 is welded at each end to an annular end member 35 of reducer 36 which is in turn welded to each end of the pipe 31. The cooling tube 33 in each pipe 31 is open at both ends so that coolant can flow freely therethrough. Each reducer 36 has a nipple 37 connecting the end of the pipe 31 to another pipe 31 or a gas line.

Each pipe 31 is filled with a suitable adsorbent 38 for effecting the separation. For separating hydrogen isotopes, the preferred adsorbent is 5A molecular sieves. Each pipe 31 as described herein is filled with about 5 kg of the 5A molecular sieves.

In order to suspend the pipes 31 in a bath of coolant within the pressure vessel 27, a support frame 40 is provided which comprises a bottom support plate 41 having holes for receiving the reducers 36 and supporting the shoulders 42 of the pipe ends, and a central rod 43 connected at one end to the plate 41 and near the opposite end to the cover 45 of the pressure vessel 27. These connections are made preferably by welding. The support frame 40 also preferably has a second support plate 47 located midway along the rod 43 having holes sized to receive the pipes 31. The plate 47 is also preferably welded to the rod 43. The pipes 31 being joined at the bottoms thereof by a connector tube 48 attached to the respective nipples 37 of the reducers 36 provide a column section 20 having a length of 12–14 feet. By adding additional lengths of pipe 31 to this basic column structure and joining those additional lengths of pipe 31 in series, a column of any desired length can be constructed.

The column section 20 is contained in a pressure vessel 27 sized to allow complete submersion of the column section 20 in liquified gas coolant with sufficient room being provided at the top of the vessel 27 to allow for 12 to 18 inches of space above the top of the coolant. The preferred coolant for hydrogen isotope separations is liquid nitrogen. The liquid nitrogen is fed into the vessel 27 through a pipe 51 branching from an outlet pipe 52 extending from a pressurized liquid nitrogen storage vessel 54 (see FIG. 2). The level of liquid nitrogen in the vessel 27 is maintained by a conventional level control 56 which governs the operation of a valve 57 on the inlet pipe 51.

The pressure vessels 27–29 are all insulated to conserve consumption of liquified gas coolant. Preferably, the vessels 27–29 are vacuum jacketed as shown in FIG. 4 where it can be seen that the vessel 27 comprises an inner wall 59 and an outer wall 60 having a space therebetween which is evacuated to a high vacuum to provide efficient insulation for a low temperature coolant such as liquid nitrogen contained within the vessel 27. The vessels 27–29 are provided with covers such as the cover 45 shown in FIG. 4, which engage the body of the vessels 27–29 to form a seal for the interior of the vessels 27–29 capable of maintaining a pressure of at least 3500 kPa. The cover 45 is provided with various fittings as schematically shown in FIG. 4 for entry and exit of the various tubes and instruments which are required to operate the column section 20 contained within the vessel 27.

As mentioned, the temperature of the column section 20 is varied by varying the pressure in the vessel 27 and hence, the boiling point of the liquid nitrogen coolant. The coolant is maintained at its boiling point by heating means 61 schematically shown in FIGS. 3 and 4. Also, the column section 20 in the first vessel 27 is heated by a flow of carrier gas which is cooled from ambient to the column temperature by flowing through the coil of tubing 63 located about the bottom of the column section 20 prior to entry into the column section 20. Generally, this heat exchange between the incoming carrier gas and the coolant at the coil 63 is sufficient to maintain the coolant boiling without the need to resort to use of a heater 61. Of course, the other vessels 28 and 29 in the column system 4 will require heaters 61, such as electrical heaters, to maintain coolant boiling. Boiling coolant also has the advantage of being self agitating, thus promoting coolant circulation through the cooling tubes 13.

Temperature in the vessel 27 is monitored by a temperature sensing means 67. The pressure in the vessel 27 is controlled by a pressure control loop 69 comprising a pressure transducer 70, a programmable controller 71, and a control valve 72 (FIG. 3). The transducer 70 monitors the actual pressure in the vessel 27 and is connected to the controller 71 which activates the control valve 72 through a current pressure converter 73 to release pressure in the vessel as required to maintain the programmed pressure. At 1 atmosphere pressure, liquid nitrogen boils at 77 K. or −196° C. By allowing the pressure to build in the pressure vessels 27 through vaporization of the liquid nitrogen, the boiling point will also rise, thereby enabling the control of the pressure within the vessel 27 to control the temperature of the boiling liquid nitrogen within the vessel 27. The vessel 27 may be pressurized up to 3500 kPa, and in practice maximum pressure of 2500 kPa or a boiling liquid nitrogen temperature of 121 K. was used.

A more complete application of the invention may be had from the following examples of the embodiment described above used for separation of mixtures of hydrogen isotopes.

EXAMPLE 1

A mixture of 50/50 H and D with up to 5 mCi/L of T was equilibrated in the presence of palladium and then mixed with about 4 mCi of pure $T_2$. Thus, the sample contained all six dimeric isotope species, with the tritium containing species being present in very low quantities.

A sample mixture of 68 normal liters (NL) was injected from the sample loop 3 into the column system 4.

The first pressure vessel 27 was initially maintained at 101 kPa or 77 K. for three hours after injection of the sample mixture onto the column section 20. The flow rate of carrier gas, which in all cases described herein was helium, was 50–60 NL/min. At this temperature the hydrogen isotopes are very strongly retained, and thus, hardly move through the 5A molecular sieve adsorbent, so a temperature increase was needed to commence the chromatography. The pressure in the vessel 27 was increased to 1960 kPa or 116 K., and elution from the column section 20 was monitored by a gas steam take-off 75 located at the exit end of the column section 20 (FIG. 3), whereby a gas stream of 30 ml/min was diverted to the detector system 7. In this manner, elution from the column section 20 began about 9 hours after injection and the total elution time was about 9 hours.

The pressure in the next pressure vessel 28 was maintained at atmospheric, i.e., 101 kPa, until the entire sample was eluted from the column section 20 and was loaded onto the column section 21, which comprised four pipes 31 joined in series. The pressure in the vessel 28 was increased to 1960 kPa or 116 K., and the sample began to emerge from the column section 21, as recorded from the takeoff 76 at the section end, at about 23 hours after inital injection with an elution time of 8 hours for the entire sample.

The temperature in the third pressure vessel 29 was maintained at 90 K. or 380 kPa during sample elution from the column section 21, and the temperature was then increased to 115 K. or 1850 kPa pressure for the separation of the sample on the third column section 22 which comprised eight lengths of pipe 31 joined in series. Again, elution was monitored via a gas stream from a take-off 77 located at the exit end of the section 22. Elution commenced 36 hours after initial sample injection, and elution required about 7 hours. Therefore, the total time for eluting the sample from the column system 4 was about 43 hours.

The separation data for this example is set out in Table 1 where separation efficiency is measured as the number of theoretical plates (NTP) derived from the following formula:

$$NTP = 16\left[\frac{t_2}{t_3 - t_1}\right]^2$$

where
- $t_1$ is the time the species starts to emerge;
- $t_2$ is the time at which the species concentration peaks on elution; and
- $t_3$ is the time when the species has been eluted from the column section.

TABLE 1

| Vessel | Start Temp. | Temp. inc. at hr. | Final Temp. | $H_2$ | HD | HT | $D_2$ | DT | $T_2$ |
|---|---|---|---|---|---|---|---|---|---|
| 27 | 77K | 3 | 116K | 410 | 130 | 440 | 260 | 490 | 2420 |
| 28 | 77K | 17.8 | 116K | 5870 | 4550 | 15600 | 4360 | 14100 | 17100 |
| 29 | 90K | 27.5 | 115K | 10600 | 6230 | 30300 | 7360 | 19200 | 14000 |

The first column section 20 successfully separated all six species, but the chromatogram shows that there was significant overlapping of species eluted and the tritiated species all exhibited very broad bases. The species which emerged from the second column section 21 showed much sharper peaks, especially for the tritiated species. Near baseline separation was obtained for HD and $D_2$. The separation of species improved only slightly for the species emerging from the third column section 22 as compared to the second section 21.

From the foregoing results, it will be apparent to the skilled person that the present column system 4 has a high degree of flexibility regarding the operating conditions which may be employed. The system 4 may be operated as two column sections instead of three by running sections 20 and 21 at the same temperature.

The column system 4 may be easily adapted to perform heart cutting techniques. In view of the excellent separation achieved at the outlet of the second column section 21, major components may be heart-cut at the exit of the second section 21, thereby enabling the column system 4 to handle a larger quantity of material and enabling a more efficient separation of species loaded onto the third column section 22. In the case of fusion fuel clean-up, heart cutting can be usefully employed to remove $H_2$ at the end of the second column section 21. Since $H_2$ is the first species eluted, followed by HD then HT, the eluting gas stream can be monitored with a beta detector for the initial emergence of HT as a means for determining which species shall be loaded onto the third column section 22 from the second section 21. This type of heart cutting allows for the removal of a major portion of the H-containing species from the fusion fuel before loading of the fuel mixture onto the final column section 22.

EXAMPLE 2

A very large sample mixture of 138 ML prepared as in Example 1 was injected into the column section 20. In this example column sectionsn 20 and 21 were operated at the same temperature at all times so these two sections performed as a unit. The vessels 27 and 28 were held at 77 K. for the first 6 hours then increased to 116 K. (1960 kPa). The carrier gas was maintained at 50–60 NL/min.

The heart cutting technique was used at the outlet of the second column section 21 to remove most of the $H_2$ and a large portion of the HD species. The remaining mixture eluted from the section 21 was loaded onto the column section 22 which was at 85 K. (240 kPa). The temperature in the column section 22 was gradually increased to 116 K. (1960 kPa). The elution data for species emerging from sections 21 and 22 are shown in Table 2. The chromatogram of the material eluted from the third column section 22 showed that only a trace of $H_2$ remained in the sample. The separation between HD and $D_2$ was close to baseline, and in general, the separation of the various species had not significantly deteriorated as compared with the 68 NL sample size of Example 1.

TABLE 2

| Vessel | Start Temp. | Temp. inc. at hr. | Final Temp. | NTP | | | | | |
|---|---|---|---|---|---|---|---|---|---|
| | | | | $H_2$ | HD | HT | $D_2$ | DT | $T_2$ |
| 27,28 | 77K | 6 | 116K | 310 | 73 | — | 790 | — | 11400 |
| 29 | 85K | 25.8 | 116K | 24300 | 7870 | 21400 | 5310 | 12600 | 59200 |

EXAMPLE 3

The use of the column system 4 for the separation of a mixture containing a relatively large amount of tritium is demonstrated by this example. A mixture of 1.25 NL hydrogen, 1.25 NL deuterium and 0.276 NL (740 Ci) tritium were equilibrated in the presence of palladium at room temperature and injected into the first column section 20. The first and second sections 20 and 21 were operated under the same conditions, namely, 77 K. for 4 hours and then 116 K. (1960 kPa) until all species had eluted. The third section 22 was maintained at 82 K. (170 kPa) during loading of the column section 22 and for about 2 hours thereafter. Then the temperature was increased to 116 K. (1960 kPa) for the remainder of the chromatography.

The separation data for species eluting column sections 21 and 22 is shown in Table 3. The chromatograms indicate that the HT and DT peaks decrease significantly at column section 22 as compared to section 21, whereas the $T_2$ peak is much larger at the end of column section 22. This suggests that some dissociation is occurring in the third column section 22, but any problems which this may cause should be surmountable by varying the conditions and recycling desired fractions for further purification.

TABLE 3

| Vessel | Start Temp. | Temp. inc. at hr. | Final Temp. | NTP | | | | | |
|---|---|---|---|---|---|---|---|---|---|
| | | | | $H_2$ | HD | HT | $D_2$ | DT | $T_2$ |
| 27,28 | 77K | 3 | 116K | 2250 | 6310 | 4540 | 8570 | 7270 | 6250 |
| 29 | 82K | 25 | 116K | 19800 | 25900 | 37600 | 29000 | 11000 | 26800 |

It will be appreciated by the skilled person that the invention described above has a great deal of inherent flexibility, and the embodiment particularly described may be modified to suit a variety of applications, yet be within the scope of the invention defined in the following claims.

We claim:

1. A low temperature gas chromatography apparatus, comprising:
   a column packed with a solid adsorbent material, having an inlet and outlet formed at either end so that a pressurized gas may be flowed through the column;
   a tube being open at both ends extending centrally through the length of the column;
   a pressure vessel sized to contain the column immersed in a liquified gas, the vessel having pressure regulating means, an inlet for liquified gas, and an inlet and an outlet for the gas being flowed through the column; and
   heating means within the vessel for increasing the temperature of the liquified gas contained therein.

2. An apparatus as claimed in claim 1, wherein the column comprises a plurality of pipe sections joined end to end in series, each pipe section having a tube extending centrally through its length, and each tube being open at both ends.

3. An apparatus as claimed in claim 2, wherein the plurality of pipe sections are apportioned among a plurality of pressure vessels, each vessel containing at least one column pipe section and the column sections so apportioned being joined from vessel to vessel in series to provide one overall column.

4. An apparatus as claimed in claim 1, wherein the column comprises one or more pipe sections of uniform internal diameter of about 3 inches.

5. An apparatus as claimed in claim 4, wherein each tube extending through each pipe section has an internal diameter of about 0.75 inch.

6. An apparatus as claimed in claim 1, wherein the column and tube are made of stainless steel or copper.

7. An apparatus as claimed in claim 1, further comprising a frame for suspending the column in the pressure vessel.

8. An apparatus as claimed in claim 7, wherein the pressure vessel has a cover to which the frame for the column is attached.

9. An apparatus as claimed in claim 1, wherein the pressure vessel is capable of being pressurized to about 3500 kPa.

10. An apparatus as claimed in claim 1, wherein the pressure vessel is insulated.

11. An apparatus as claimed in claim 10, wherein the pressure vessel comprises an inner and an outer wall and the insulation is a vacuum provided between the walls.

12. An apparatus as claimed in claim 1, wherein the pressure regulating means for the pressure vessel comprises a pressure transducer, a programmable controller and a control valve, the transducer monitoring the actual pressure in the vessel and being connected to the controller which activates the control valve to maintain the programmed pressure.

13. An apparatus as claimed in claim 1, wherein the heating means comprises a tube positioned within the vessel for cooling a carrier gas from ambient temperature to the temperature within the vessel, the tube being connected at one end to the inlet of the column and at the other end to the carrier gas supply.

14. An apparatus as claimed in claim 1, wherein the heating means is an electrical heater.

15. An apparatus as claimed in claim 1, wherein the column is packed with a molecular sieve material.

16. An apparatus as claimed in claim 1, wherein the column is made of copper.

17. A low temperature gas chromatography apparatus, comprising:
- a column packed with a solid adsorbent material, having an inlet and outlet formed at either end so that a pressurized gas may be flowed through the column, the column being divided into at least two sections, all of which are connected in series;
- a plurality of pressure vessels, each vessel being sized to contain a column section immersed in a liquified gas, each vessel having pressure regulating means, an inlet for liquified gas, and an inlet and outlet for the gas being flowed through the column section; and
- heating means within each pressure vessel for increasing the temperature of the liquified gas contained therein.

18. An apparatus as claimed in claim 17, wherein each column section comprises a plurality of substantially straight pipe sections joined end to end in series.

19. An apparatus as claimed in claim 17, wherein the column comprises stainless steel or copper pipe.

20. An apparatus as claimed in claim 17, further comprising a frame for suspending each column section in a pressure vessel.

21. An apparatus as claimed in claim 20, wherein each pressure vessel has a cover to which the frame for the column section is attached.

22. An apparatus as claimed in claim 17, wherein each pressure vessel is capable of being pressurized to about 3500 kPa.

23. An apparatus as claimed in claim 17, wherein each pressure vessel is insulated.

24. An apparatus as claimed in claim 17, wherein the pressure regulating means for each pressure vessel comprises a pressure transducer, a programmable controller and a control valve, the transducer monitoring the actual pressure in the vessel and being connected to the controller which activates the control valve to maintain the programmed pressure.

25. An apparatus as claimed in claim 17, wherein the heating means comprises a tube positioned within a vessel for cooling a carrier gas from ambient temperature to the temperature within the vessel, the tube being connected at one end to the inlet of the column and at the other end to the carrier gas supply.

26. An apparatus as claimed in claim 17, wherein the heating means is an electrical heater.

27. An apparatus as claimed in claim 17, wherein the column is packed with a molecular sieve material.

* * * * *